United States Patent [19]

Barker et al.

[11] 4,426,542

[45] Jan. 17, 1984

[54] SYNTHESIS OF PLASTICIZER AND DETERGENT ALCOHOLS

[75] Inventors: George E. Barker; Denis Forster, both of St. Louis, Mo.

[73] Assignee: Monsanto Company, St. Louis, Mo.

[21] Appl. No.: 272,587

[22] Filed: Jun. 11, 1981

Related U.S. Application Data

[63] Continuation-in-part of Ser. No. 256,439, Apr. 22, 1981, which is a continuation of Ser. No. 104,517, Dec. 17, 1979.

[51] Int. Cl.$^3$ .............................................. C07C 29/14
[52] U.S. Cl. .................................... 568/883; 568/451; 568/463; 568/876; 568/878; 568/882; 568/909
[58] Field of Search ............... 568/451, 454, 882, 883, 568/876, 878, 463, 909, 451, 464

[56] References Cited

U.S. PATENT DOCUMENTS

| | | | |
|---|---|---|---|
| 2,684,385 | 7/1954 | Biribauer et al. | 568/463 |
| 2,842,514 | 7/1958 | Bartlett et al. | 568/451 |
| 2,852,563 | 9/1958 | Hagemeyer et al. | 568/451 |
| 2,921,089 | 1/1960 | Hagemeyer et al. | 568/882 |
| 3,119,876 | 1/1964 | Jaros et al. | 568/451 |
| 3,127,451 | 3/1964 | Berkeley | 568/882 |
| 3,952,068 | 4/1976 | Gipson et al. | 568/463 |
| 4,032,578 | 6/1977 | Savini et al. | 568/464 |
| 4,263,449 | 4/1981 | Saito et al. | 568/909 |

OTHER PUBLICATIONS

Johnson, "J. Chem. Society" (1963) pp. 4859–4864.

*Primary Examiner*—Werren B. Lone
*Attorney, Agent, or Firm*—Joseph D. Kennedy; James W. Williams, Jr.

[57] ABSTRACT

A preparation of a plasticizer alcohol, consisting of predominantly 2-propylheptanol, from linear butenes is described in which oxo product of the butenes is aldoled to condense n-pentaldehyde therein with very little cross-aldolization followed by hydrogenation to obtain the 2-propylheptanol with very small 2-propyl-4-methyl hexanol content. The alcohol product as phthalate ester has excellent plasticizer properties. Also processes are described for converting other olefins to alcohols by oxo, aldol and hydrogenation reactions, with particular attention to converting hexenes obtained by propylene dimerization to $C_{14}$ alcohols suitable for preparation of detergents.

23 Claims, No Drawings

SYNTHESIS OF PLASTICIZER AND DETERGENT ALCOHOLS

This application is a continuation-in-part of our application Ser. No. 256,439, filed Apr. 22, 1981 as a continuation of Ser. No. 104,517, filed Dec. 17, 1979.

The present invention is concerned with preparing alcohols from olefin feedstock.

The present invention is further concerned with preparing ten-carbon plasticizer alcohols from substantially linear butene feedstock.

BACKGROUND OF THE INVENTION

Various lower olefinic stocks are available from petroleum sources, and many procedures are known for converting lower olefins to high olefins, or to higher molecular weight compounds with various functional groups. Among such procedures are catalytic dimerization procedures for converting propylene and butenes to heptenes and octenes respectively and such dimers can be catalitically hydroformylated to aldehydes, which can be reduced to alcohols. Lower olefins can be hydroformylated, using rhodium, cobalt, or other catalysts, to the corresponding aldehydes. Aldehydes in turn can be converted to higher aldehydes by the well known aldol reaction, such as that taught in U.S. Pat. No. 2,921,089 for converting n-vale aldehyde to 2-propyl-2-heptanol, and then hydrogenated to 2-propylheptanal and 2-propylheptanol. It is also known that various alcohols can be utilized to esterify phthalic acid to form useful plasticizers, e.g. 2-ethylhexanol, 2-propylheptyl alcohol, decyl alcohols, etc. as disclosed in the aforesaid U.S. Pat. No. 2,921,089. It is also known to conduct an aldol reaction of mixtures of normal and branched aldehydes under conditions which force cross aldol reaction of the branched aldehyde with the normal aldehyde, see U.S. Pat. No. 2,852,563.

Among dimerization processes is the Dimersol® dimerization process for dimerizing olefins using a nickel coordination complex and an aluminum alkyl as catalyst. The process can convert propylene to hexenes with selectivity in excess of 85%. The hexenes can be converted by oxo reaction to aldehydes and then alcohols, producing heptanols. M. Johnson has studied oxo reaction of 4-methylpen-1-ene, showing migration of the double bond during the reaction, and fairly large production of a 2-substituted aldehyde, 2,4-dimethylpentanal, along with 5 methyl-hexanol as the main product (J. Chem. Soc. 1963, 4859).

Reactions of the type described characteristically produce mixtures of isomeric products. Therefore in the production of plasticizer alcohols, distillations may be employed at an early stage to separate isomeric materials. An alternative is to effect selective reaction of the isomeric materials with resulting effect upon product properties.

SUMMARY OF THE INVENTION

The present invention involves a process in which mixed butenes are converted to a ten-carbon plasticizer alcohol comprised of at least about 80%–90% 2-propylheptanol by an oxo reaction of the butenes to obtain amyl aldehydes with at least about 66% n-pentaldehyde content, followed by an aldol reaction of the aldehydes under conditions to cause substantially all of the n-pentaldehyde to react but with incomplete conversion of branched aldehydes, and then hydrogenating to produce alcohols in which the ten-carbon alcohols are comprised of at least 80%–90% 2-propylheptanol. Under the aldol conditions employed the 2-methylbutanal present does not readily condense with itself, and condenses at a comparatively slow rate with the n-pentanal, so that the 2-propyl-4-methylhexanol content (resulting from the so-called cross aldol of n-pentanal with 2-methyl-butanal) in the resulting alcohol is held to no more than about 15–20%, often 12% or less. The ten-carbon alcohol mixture, after isolation from other components, is admirably suited as a plasticizer alcohol, having good plasticizing properties as the phthalate diester. It approaches the excellent plasticizer properties of the 2-propylheptyl phthalate, as the small amount of 2-propyl-4-methylhexanol causes only a slight decline in such properties.

The described procedure is advantageous in that it avoids the expense of a fractionation of difficultly separable aldehyde isomers prior to the aldol reaction, and produces an excellent plasticizer alcohol in high yield by an efficient procedure from the source materials. The main side product, 2-methylbutanol, is in itself useful as a plasticizer alcohol. The invention utilizes selective aldol reaction as a step in producing a quality plasticizer alcohol without normally requiring separation of aldehyde isomers prior to aldol condensation. This contrasts with the procedure used in 2-ethylhexanal manufacture in which propylene is hydroformylated to a mixture of n-butanal and 2-methylpropanol (isobutyraldehyde), and the mixture of close boiling isomers is then carefully separated by fractional distillation in an expensive multiple tray column, so that the n-butanal can be taken forward to an aldol reaction.

The invention is further concerned with process in which olefins selected from those with 3 to 7 carbon atoms are converted to aldehydes with 4 to 8 carbon atoms, which are then subjected to aldol condensation to obtain aldol products in relatively high yield for hydrogenation to alcohols having useful properties and derivative uses, with especial interest in conversion of hexenes to heptanals and to $C_{14}$ alcohols for use in detergents.

DETAILED DESCRIPTION OF THE INVENTION

In the production of plasticizer alcohols from olefins, typical procedures introduce branching into the alcohol product. The branching has a significant effect upon properties when the alcohols are utilized as plasticizers in the form of phthalate esters. It is therefore desirable to control the degree of branching.

The present invention utilizes an oxo reaction of olefins, followed by an aldol condensation. If n-pentanal is reacted in an aldol condensation, followed by hydrogenation, 2-propylheptanol is obtained, and is well-suited as a plasticizer alcohol. If n-pentanal is reacted in a cross-aldol reaction with 2-methylbutanal, the alcohol obtained following hydrogenation is 2-propyl-4-methylhexanol, which has much poorer properties as a plasticizer alcohol. It follows that a superior product can be obtained by separating n-pentanal from its isomers prior to conducting the aldol reaction. However, isomeric aldehydes have similar boiling points, and separation by distillation on a commercial scale involves high capital cost equipment with consequent expense together with a very substantial energy cost. In the presently described invention there is great advantage in avoiding such a distillation step.

The present invention in one particular aspect employs an oxo reaction of butenes to obtain a mixture of aldehydes, which is then subjected to an aldol reaction. The oxo reaction involves contacting substantially linear butenes with hydrogen and carbon monoxide and hydroformylation catalyst under hydroformylation conditions suited to obtaining a high proportion of n-pentanal in the aldehyde product. It is desirable to have the n-pentanal to branched aldehyde ratio at least about 2.0:1, representing at least about 66.7% n-pentanal content. Aldehydes with 70–75% normal content, or even higher normal contents are desirable to the extent available from oxo reactions, possibly up to 85%, and will be useful for the aldol stage of the present invention.

The aldol reaction is carried out utilizing the usual aldol catalysts and conditions to promote the aldol reaction of the n-pentanal, using elevated temperatures upwards of 60° C., particularly temperatures of about 90° C. to 130° C., or possibly up to 150° C. or higher if desired. The reaction is operable over broad pressure ranges including pressures less than atmospheric as well as elevated pressures, but will usually be effected at slightly elevated pressures sufficient to maintain the reactants substantially in the liquid state. The reaction can also conveniently be conducted at reflux. The conditions and parameters discussed and illustrated herein with respect to butenes and pentanals are in general exemplary of those for other olefins and aldehydes.

Under the aldol conditions employed, the n-pentanal reacts with itself to form aldol product at a rate about 15 times greater than it reacts with 2-methylbutanal. The aldol reaction is permitted to go to 80% or so completion so that if about 25% of the aldehyde supplied is 2-methylbutanal, about 3/4 of it will remain unreacted, and about 88% of the aldol product will be that from self-condensation of n-pentanal. The conversion of n-pentanal to aldol product will be very high and desirably nearly complete, such as upwards of 90 or 95%. There will be some variation with conditions and isomer content of the aldehydes utilized, but the present invention contemplated obtaining aldol product with about 80% to about 95% being from the self-condensation of n-pentanal, and preferably at least 85% from self-condensation with no more than 15% of 2-propyl-4-methylhexanal being produced. In the present process, the aldol intermediate, 2-propyl-3-hydroxyl-heptanal will ordinarily be dehydrated in the aldol procedure to 2-propylheptenal. Under some conditions the immediate aldol product can be isolated, but ordinarily under the temperature conditions employed herein the 2-propyl-2-heptenal is produced. The aldol reaction can utilize strongly alkaline catalyst, such as sodium and potassium hydroxide, or sodium and potassium cyanide. The concentration of the aqueous alkali can be varied, but molar or similar concentrations of alkali metal hydroxides can be used, and concentrations selected will generally be in the range of about 1 to 10% by weight. The amount of aqueous alkali to aldehyde reactant can also vary, for example from about 15% by volume aqueous alkali up to about 75% by volume aqueous alkali. The aldol reaction will be run for a sufficient time to obtain the desired degree of conversion, which for batch reactions may be in the range of about 1 to about 3 hours, while in continuous reaction times of less than five minutes are achievable. The reaction is stopped by permitting the reaction mixture to cool and separating the organic reaction phase from the aqueous alkali phase. Since the n-pentanal reacts more rapidly than its isomers, the proportion of the isomers in the unreacted aldehyde increases, and it therefore is not generally desirable to separate and recycle unreacted components to the reaction.

For the oxo reaction, linear butene streams are available which may have up to 70% 1-butene with the balance 2-butene. Butene streams generally contain isobutylene also, but the isobutylene can be separated in a reaction with methanol producing methyl tertiary butyl ether, making linear butenes available which are substantially free of isobutylene. The hydroformylation procedures described herein can be employed to obtain aldehydes with a great predominance of the n-pentanal from linear butenes containing even a high proportion of 2-butene, as even 2-butene itself produces a pentanal: 2-methylbutanal ratio of about 2.33, and a 1:2 mixture of 1-butene:2-butene produces product ratios in the range of about 2.8:1 to 3.1:1. In terms of available and effective materials, it may be desirable to employ linear butene mixtures in which 1-butene is from $\frac{1}{3}$ to $\frac{1}{2}$ of the mixtures; and, of course, higher proportions of 1-butene could be used if available, up to 100% 1-butene. It happens, however, that the amount of normal aldehyde product is not very sensitive to increases in the 1-butene content in ranges above 50%.

It is important that the hydroformylation of the mixed linear butenes gives a relatively high ratio of normal aldehydes, as this contributes to the feasibility of using the aldehyde mixture for an aldol reaction to obtain a fairly high yield of 2-propylheptanal (and ultimately 2-propylheptanol) without excessive 2-propyl-4-methylhexanal. The use of moderate temperatures in the hydroformylation contributes to obtaining about a 3:1 mixture of normal to branched aldehyde. Thus temperatures sufficient to produce an appreciable reaction rate, ranging from 80° to 100° C. or so can be used, and temperatures on up to 125°–130° C. can be employed to obtain better reaction rates. Still higher temperatures up to 150° C. or higher can be used but with a tendency to produce more branched aldehyde than desired. To some extent high catalyst concentrations can be employed to obtain reaction rates, even at relatively low temperatures. Cobalt catalyst is especially suited to obtain the desired high proportion of normal aldehyde. Unmodified cobalt carbonyl catalyst can conveniently be used. Such catalyst, conventionally designated as cobalt octacarbonyl, can be provided or employed in many forms known to be useful as a hydroformylation catalyst, although it may be necessary to exercise some choice to provide catalyst best suited to obtaining a high proportion of normal product.

The oxo stage of the reaction can be conducted under the usual conditions pertaining to cobalt catalyzed hydroformylation reactions, with attention to the temperature conditions as described above. Usual pressure conditions apply, such as 1000–4000 or up to 5000 psi total pressure, with most of the pressure being from the carbon monoxide and hydrogen supplied. The carbon monoxide and hydrogen are conveniently used in 1:1 ratio and obtained from usual synthesis gas sources, but other ratios can be employed in keeping with known hydroformylation practice. The reaction can be carried to the desired stage of completion in 1 to 3 hours or so on a batch basis, varying with time, temperature, pressure and catalyst concentration.

The reaction can be conveniently conducted either without a solvent or with solvents and, employing concentrations customary for homogeneous catalyst reactions, such as 2 to 10 molar or greater concentrations of the butenes in a solvent, e.g., hydrocarbon solvents such as toluene, and 0.1% to 1% by weight, based on cobalt, of catalyst.

The present invention is also concerned with preparing detergent range alcohols from propylene feedstock. The detergent range alcohols are somewhat higher in carbon number than plasticizer alcohols, often having about 14 carbon atoms, but in some cases ranging from about 11 to about 16 or so carbon atoms. Propylene can be dimerized to hexenes, and the hexenes can be converted to aldehydes by an oxo reaction as described herein, and the resulting heptaldehydes can be reacted in an aldol reaction to produce aldol products which can be hydrogenated to $C_{14}$ alcohols.

The described route to $C_{14}$ alcohols gives an alcohol having properties suitable for use in preparing detergents. While the alcohols have some branching, much of the product is mono-branched, or of a branched structure which can be biodegraded. Thus, depending upon particular procedures utilized, the product may be comprised in large part of 2-pentylnonanol, possibly with a small fraction of 2-pentyl-4-methyloctanol. Such structures, with non-adjacent branches, are susceptible to biodegradation.

For reactions where the ultimate product is a plasticizer, as usual in those involving aldol reactions of pentanals, there is interest in limiting cross-aldol reactions which increase chain branching. However, for other uses where branching is not necessarily detrimental, some cross aldol reactions are useful as augmenting the efficient utilization of feed stock materials. Thus in a broader sense the present invention can utilize aldol reactions in which there is aldol and crossaldol condensation of n-aldehydes along with branched aldehydes in which the branching is not at the 2-position, or generally including the class of alkanals except for those with substituted on the 2-position. This applies to aldehydes with 4 to 8 carbon atoms, as obtainable from oxo reactions of $C_3$ to $C_7$ olefins, and applies particularly to aldehydes with 6 to 8 carbon atoms. Thus in such aldol reactions, crude oxo mixtures containing a number of isomers may be employed, and substantially complete reaction of all the aldehydes except the 2-substituted aldehydes can be achieved. For example, better than 95% conversion of α-aldehydo alkanes can be achieved, while conversion of 2-substituted aldehydes may be in the neighborhood of 25 to 30% or possibly even up to 50%. Thus it is feasible to use such crude oxo mixtures in aldol reactions to obtain useful products. Using oxo product in which the α-aldehyde alkane content may range from 60 up to near 80% or so, aldo conversions may approach 75 to 90%, even though participation of the 2-substituted aldehydes is limited, so that it is involved in cross-aldol producing no more than 20% of the product.

It is possible to obtain butene streams which are substantially linear and substantially free of isobutylene, in which no more that 2% or so of the butenes is isobutylene, and it is advantageous to use such butene streams. However, somewhat more isobutene can be tolerated, so long as the total of the resulting 3-methylbutanal together with other branched aldehydes in the aldehydes to be reacted does not become undesirably high. The 3-methylbutanal is more prone to react in the aldol reaction than the 2-methylbutanal isomer, so it is desirable to keep its presence to a minimum.

The hydrogenation of the enals from the aldol reaction can be conducted under the usual catalytic hydrogenation conditions for reducing olefinic bonds and aldehyde groups. The carbon-to-carbon bond reduce more rapidly and at a lower temperature than the aldehyde group, e.g. at about 90° C., with cobalt on Kieselguhr catalyst at elevated hydrogen pressure. The hydrogenation will generally be carried out at 500-2000 psi, or greater hydrogen pressures and temperatures of 130° to 200° C. or higher, although any temperatures which are effective with a particular catalyst can be used. The stated conditions will be effective for reducing both the carbon-to-carbon bond and the aldehyde group to obtain saturated alcohol. Various other hydrogenation catalysts can be used including platinum and platinum on carbon catalysts, copper chromite, activated nickel etc., and individual catalysts can be utilized in conjunction with other catalysts.

The present invention involves an oxo reaction, followed by an aldol reaction, and then a hydrogenation to convert enals to alcohols. For large scale operations, the oxo reaction will be conducted with usual provisions for separating gaseous reactants and products, and catalyst, from the aldehyde products, with recycle as appropriate. The aldehyde product mixture will then be subjected to an aldol reaction, followed by decantation and water washing or other simple procedures to separate the organic product-containing phase from the aqueous phase. The product phase is then hydrogenated, converting both the $C_5$ aldehydes and $C_{10}$ enals to the corresponding alcohols. The hydrogenation is followed by a distillation to remove light ends, followed by a distillation to remove $C_5$ alcohols. Both the $C_5$ and $C_{10}$ alcohols can then be treated in further hydrogenation polishing operations to improve the alcohol quality by insuring complete hydrogenation. The ten-carbon alcohol mixture thus obtained will, as described herein, have a high content of 2-propylheptanol with only small amounts of 2-propyl-4-methylhexanol or other branched alcohols, the amounts of such materials being sufficiently small that the alcohol mixture has properties suitable for a plasticizer alcohol.

The five-carbon alcohol co-product obtained is principally 2-methylbutanol, a useful product; historically five-carbon alcohols have more value than ten-carbon alcohols. The separation of the five-carbon from ten-carbon alcohols is readily effected by distillation in equipment constructed of inexpensive alloys such as carbon steel. Separation at this stage is simple, compared to the difficult separation which would be required to separate the five-carbon aldehyde isomers prior to the aldol reaction.

As an alternate to the above procedure, it is possible to separate the five-carbon aldehydes by distillation from the 10-carbon enals prior to hydrogenation. For convenience of separation, distillation of the alcohols is generally preferred, and then the five-carbon components are in the form of alcohols. However, if the aldehydes are desired for some purpose, separation is appropriate, and this has the advantage of avoiding unnecessary hydrogen use.

Hexenes, as produced by dimerization of propylene with transition metal catalysts, as in the Dimersol ® dimerization process, are characterized by being composed almost entirely of internal olefins, and a linear content generally reported as about 20%, but ranging up to 29% or so. The main isomer present is a 2-methyl- 2-pentene, along with other 2- and 4-methyl pentenes and around 6% 2,3-dimethyl-2-butene.

The linear hexenes can be separated from the crude dimerization product by use of a molecular sieve or other suitable procedure, and the linear hexenes alone then subjected to an oxo reaction to obtain heptanal products, with the linear content of the heptanals ranging up to 75% or more. Branched isomers which may be present include 2-methylhexanal, and 2-methylpentanal. The oxo product mixture can be reacted in an aldol reaction, employing aldol conditions as described herein, to product aldol products. Under the aldol conditions employed, the n-heptanal reacts with itself at a rate about 10–15 times faster than it reacts with 2-methylhexanal or other 2-substituted aldehydes. Thus, when the $C_7$ aldehydes are produced from linear hexenes, a product compound predominantly of product from self-condensation of n-heptanal can be obtained by carrying out an aldol reaction of the oxo reaction product, with some control over the amount of product from 2-substituted aldehydes by controlling the amounts of conversion which is permitted. It may be desirable to have better than 50 or 60% completion for efficient use of feed stock, and conversions of 80% or higher may at times be desirable. The reaction can be run to achieve 95% or better conversion of the n-aldehyde to aldol product, while only about ¼ to ⅓ or so of the 2-substituted aldehydes are usually converted to aldol products by a cross-aldol reaction. With use of appropriate control, aldol product with about 80% to say 95% from self-condensation of n-heptan 1 can be obtained, for example at least 85% from self-condensation, with no more than 15% of cross-aldol product. Depending upon the properties desired in the product, the degree of branching can be controlled to a considerable extent by the present process. It happens that some known detergent range alcohols have a fair degree of brancing and still have satisfactory biodegradability Regardless of the desired degree of branching, there is advantage in being able to carry out an aldol reaction on the oxo product of the hexenes, without need for separating branched aldehyde isomers, and obtain a useful product, particularly considering the low cost nature of the feed stock and process. The process can be used to obtain a product composed of about 85% 2-pentylnonanol and 15% 2-pentyl-4-methyl-octanol.

The oxo process can generally be utilized to achieve 90–95% yields of aldehydes. With linear hexenes as reactants, selectivity to aldehydes without 2-substituents, i.e. α-aldehydealkanes, can be as high as 60 to 65%, but in large scale operation will possibly range from 50 to 65%.

The $C_7$ branched aldehydes which do not react in the aldol reaction can be separated from the reaction mixture for various purposes, or hydrogenated with the mixture and utilized as a $C_7$ branched alcohol. If desired, the branched $C_7$ alcohol can be dehydrated, and then subjected to an oxo reaction to produce an aldehyde with an additional carbon atom. Thus 2-methylhexanol can be converted to 2-methylhexene-1, which can be recycled to the oxo stage of the reaction process and hydroformylated to predominantly 3-methylheptanal. This 3-methylheptanal, not having any substituent in the 2-position, reacts at a good rate in the aldol reaction. Other unreacted aldehydes, such as 2,4-dimethylpentanal and 2-ethylpentanal, can similarly be hydrogenated and dehydrated and recycled to be converted in the oxo stage to $C_8$ aldehydes with no substituent in the 2-position, which will take part in the aldol reaction when recycled through that stage. This procedure to use the unreacted $C_7$ aldehyde results in greater conversion of the original reactants to the desired final product, rather than to a concomitant product such as $C_7$ alcohols. Use of this recycle feature in the oxoaldol process changes the product obtained from linear hexenes considerably, and can produce a product composed on a mole basis of about 40% 1-pentyl-nonanol, about 30% 2-pentyl-5-methylnonanol, and about 10% of 2-(1-methylpentyl)-5-methyl-nonanol.

As indicated above, the linear content of propylene dimers is fairly low, being around 20% or somewhat higher. At times there may be advantage in separating the linear components for use in the present process, while the branched materials can be used in gasoline with advantage to the octane rating of the gasoline. However, it has been found that the entire hexenes portion of the propylene dimerization product can, if desired, be utilized as feedstock for the present oxo-aldol process. The branched isomers are typified by 2-methyl-2-pentene, which, when subjected to oxo reaction with cobalt catalyst, has been found to be very selectively converted to 3-methyl- and 5-methylhexanals. Fortunately it has been found that cobalt catalyst, in contrast to rhodium, has the effect of isomerizing the internal olefins so that the aldehyde group is predominantly on the end of the chain. It appears that the methyl substituent has some influence in directing the oxo reaction to obtain a great predominance of aldehydes with no substituent in the 2-position. It is very important to the use of propylene dimer in the present process, that the oxo product is predominantly an alpha aldehydoalkane, i.e. there is no substituent in the 2-position. As discussed herein, aldehydes with substituents in the 2-position do not readily undergo aldol reactions. Thus if the internal hexenes were converted largely to such unreacted aldehydes, it would be very difficult to effect self-condensation of such aldehydes to a useful extent, and the use of propylene dimers in the present oxo-aldol process would be impractical. However, as discussed herein, the oxo process with cobalt catalyst converts the hexenes largely to aldehydes which will react in the aldol reaction, making hexenes, obtained from propylene dimerization, very suitable as a feedstock for producing detergent range alcohols in accord with the present invention.

Particular branched hexene isomers are converted to -aldehydoalkanes with very high selectivity, with 2-methyl-2-pentene selectivity of 90.2% being obtainable. The mixture of both branched and linear hexenes from propylene dimerization can be converted to α-aldehydoalkanes with selectivity such as about 78%. Thus higher selectivity to aldehydes desirable for the aldol reaction can be obtained by using the crude hexenes mixture for the oxo reaction, rather than only the linear hexenes. Depending upon relative value and availability of the linear and branched hexenes, one might find advantage in using only the branched hexenes in the present process because of the high selectivity in the oxo process to -aldehydes suitable for aldol reaction.

By use of the entire hexene cut from propylene dimerization in the oxo-aldol process, followed by hydrogenation, a $C_{14}$ alcohol product can be obtained which is about 15% 2-pentylnonanol, about 10% 2-pentyl-4-methyl-octanol, about 50% 2-pentyl-7-methyloctanol, and about 25% 2(3-methylbutyl)nonanol. If branched C₇ alcohol produced from unreacted aldehyde is dehydrated and recycled to the oxo stage as discussed above, a product can then be obtained which is about 10% 2-pentylnonanol, about 5% 2-pentyl-4-methyloctanol, about 25% 2(4-methylpentyl)-7-methyloctanol, about 10% 2-pentyl-7-methyloctanol, and various multi-branched hexadecanols, e.g., 2(2-ethyl,3-methyl-propyl)-5-ethyl-6-methylheptanol.

EXAMPLE 1

An aldol reaction was conducted in a 1 liter round bottom flask equipped with stirrer, addition funnel, reflux condenser and adaptors for nitrogen flow. A 100 ml. amount of aqueous 1 molar potassium hydroxide solution was placed in the flask and heated to about 85° C. n-Pentanal and 2-methylbutanal were admixed in about 3:1 ratio, after each had been purified by distillation, and used for gradual addition to the reaction flask with stirring. Over about one hour, about 300 ml was added containing 187.7 grams n-pentanal and 60.8 grams 2-methylbutanal. The reaction mixture was placed in a separatory funnel; and the lower aqueous phase (87 grams) was separated. The organic layer was washed four times with water, and amounted to 213.5 grams. Gas chromatographic analysis for the starting aldehydes indicated about a 3:1 ratio of 2-methylbutanal to n-pentanal, showing that the n-pentanal had been consumed at a much higher rate in the reaction. The product contained about 70.5% of alkenal condensation product and 25.3% of the starting aldehydes. The product had 2-propylheptanal in about 9:1 ratio to 2-propyl-4-methylhexenal.

A 110.89 gram amount of the product was utilized for hydrogenation, employing 11 grams of cobalt on Kieselguhr catalyst with 4.4 ml H₂O as promoter, in a 300 ml stirred autoclave. The autoclave was pressured to 1000 psi with hydrogen and gradually heated, with hydrogen uptake starting at about 40° C. After one hour, the pressure had fallen to 480 psi, and the autoclave was again pressured to 1000 psi. After two hours, with further addition of hydrogen, the pressure was 1510 psi and temperature 160° C. The run was continued for a total of sixteen hours. The measured gas uptake was in very slight excess of theory for hydrogenation of both the olefin and aldehyde groups in the compounds present.

The product was filtered through a Celite filter mat to remove catalyst, and the mat was washed with n-hexane. The n-hexane was removed under vacuum, leaving 88 grams of product for distillation. Distillation was carried out at 10 mm Hg., with 18.1 gram being collected at 30°-100° C., which gas chromatography indicated to be 66.4% 2-methylbutanol, 27.5% pentanol, and 4.1% 2-propylheptanol. An additional 38.9 grams was collected at 103.5°-105° C., 11.3% 2-propyl-4-methylhexanol and 87.7% 2-propylheptanol. It can be seen that the above described procedure provides 2-propylheptanol with only very minor adulteration by the aldol alcohol product of branched aldehydes. Also the 2-propylheptanol thus produced was readily separated by distillation from the 2-methylbutanol produced by hydrogenation of the 2-methylbutanal which did not undergo the aldo condensation.

EXAMPLE 2 n-Pentanal, 246.3 grams, and 2-methylbutanal, 82.1 grams, were mixed and utilized for an aldol reaction, employing 100 ml of aqueous 1 molar sodium hydroxide. The aldehydes were added to the aqueous hydroxide in a flask as described in Example 1. The aldehyde addition took twenty minutes and the mixture was then refluxed, 89°-89.5° C., for one hour. Gas chromatographic analysis indicated that 50% of the aldehydes had reacted, and the reaction mixture contained 20.7% 2-methylbutanal, 28.6% pentanal, 4.8% 2 propyl-4-methyl-hexanal and 37.9% 2-propyl-2-heptanal. Thus it is shown that the n-pentanal (valealdehyde) reacted with itself at a much faster rate than with the 2-methylbutanal, making the 2-propyl-heptanal much more predominant as product than the 3:1 predominance of n-pentanal as starting aldehyde. The lower aqueous phase was removed and the upper organic layer was distilled under vacuum. Volatile materials, including water, n-pentanal, 2-methylbutanal, and pentanol, were removed under vacuum reaching 20 mm Hg. a total of 78 grams being collected in cold traps. Heat was then applied and 3.88 grams collected at a headt temperature of 52°-86° C., 9.93 grams at 86° C., 5.65 grams at 90° C., and an additional 26.04 grams at 90° C. All of the fractions were predominantly 2-propyl-2-heptanal, in the range of about 70 to 80%, with 2-propyl-4-methyl-hexenal constituting only a small fraction of the product. The unreacted 2-methylbutanal was, as indicated, readily separated from the much higher boiling 2-propyl2-heptanal product.

EXAMPLE 3

An aldol product mixture was utilized for hydrogenation. The product mixture was from reaction of n-pentanal and 2-methylbutanal, with the latter being in excess during much of the reaction and contained about 54% 2-rpopyl-2-heptanal and 2-propyl-4-methyl-2-hexenal in about 3:2 ratio. The hydrogenation was conducted with cobalt on kieselguhr at pressures up to about 1500 psi and temperatures from 125° to 160° C. for three and one-half hours. The product was vacuum filtered and the filter washed with hexane which was removed by vacuum. Chromatography indicated the mixture was about 35% C₅ alcohols and 60% C₁₀ alcohols. The mixture was washed with sulfuric acid diluted with an equal amount of water, and then with water several times. Distillation was then carried out using a fractionating head, obtaining 44.26 grams at 125° to 200° C. at atmospheric pressure, the fraction being 74.1% 2-methyl-1butanol and 16.3% pentanol, and slightly over 5% C₁₀ alcohols; and then 42.35 grams at 70° to 109° C. at 10 mm, with 41.8% being 2-propyl-4-methyl-1-hexanol and 52.5% 2-propyl-1-heptanol, with less than 2% C₅ alcohols; and 16.6 grams at 109°-114° C. at 10 mm, with 30.4% 2-propyl-4-methyl-1-hexanol and 66.6% 2-propyl-1-heptanol.

Thus it is demonstrated that the hydrogenated aldol condensation profuct, viz. 2-propyl-1-heptanol, is produced by hydrogenation of aldol reaction product and separation readily effected from hydrogenated product of unreacted aldehyde, 2-methyl-1-butanol.

EXAMPLE 4

A mixture of butenes was hydroformylated with cobalt catalyst. The reaction was carried out in a 300 ml stirred autoclave in 100 ml. solution with toluene as solvent and 0.3% by weight cobalt carbonyl as catalyst. Utilizing a 5 molar concentration of butenes, with 1-butene and 2-butene in 1:1 ratio and CO:H₂ in 1:1 ratio, the reactor was pressure to 2400 psi gauge and heated to 100° C. and 3000 psi gauge. After 5.2 hours, all but 6% of the olefin had reacted, producing n-pentanal and 2-methylbutanal in 2.0:1 ratio, the pentanal constituting 66.8% of the reaction mixture. The reaction rate was 2.1 grams moles per liter-hour.

EXAMPLE 5

A hydroformylation similar to Example 4 was conducted utilizing a 1-butene to 2-butene ratio of 1:2 and obtaining a n-pentanal to 2-methylbutanal ratio of 3.2 after 1 hour and 3.1 after 6-hours. In similar procedures, the ratio was in the range of 2.8:1 to 3.1:1.

EXAMPLE 6

The procedure of Example 4 was repeated but utilizing 2-butene as the olefin, to obtain a pentanal to methylbutanal ratio of 71:29 at 100° C., and 69:131 at 110° C.

EXAMPLE 7

A mixture of butenes, 1-butene:-butene:isobutylene in 1:1:2 ratio, was hydroformylated in accord with the procedure of Example 4, producing pentanal:2-methylbutanal:3-methylbutanal in 15:5.2:11 ratio after one our reaction.

the hydroformylations of butenes take place at excellent rates over cobalt catalysts and with good selectivity to aldehydes, selectivities greater than 93% being obtainable. With butene-2 as the substrate and 0.3 wt. % cobalt, (based on cobalt metal) rates over 5 gram moles per liter-hour have been observed at 110° C.

A sample of 2-propylheptanol was used to esterify phthalic acid to obtain a plasticizer. The plasticizer was used to plasticize polyvinyl chloride (PVC) and found to have good plasticizing properties, as compared with other plasticizers in Table 1.

TABLE 1

| Plasticizer | | Volatility | |
|---|---|---|---|
| (40% in PVC) | Low Temp. Flex ($T_f$) | 1 day | 6 days |
| Di(2-propylheptyl) phathalete | −40° C. | 1.0% | 3.7% |
| Dioctyl phthalate (2-ethylhexyl) | −39° C. | 3.9% | 19.0% |
| Diisononyl phthalate | −36° C. | 1.8% | 7.0% |
| Diisodecyl phthalte | −37° C. | 1.2% | 4.2% |

*Determined in a standard Clash-Berg test.

It is recognized in the Plastics Industry that the more efficient a plasticizer is, the lower the temperature in the Clash-Berg low temperature flexibility test, i.e. a $T_f$ of −45° C. indicates a far superior plasticizer than a $T_f$ of −35° C. Therefore in the above table it can be seen that the propylheptyl phthalate compares favorably, having a lower flexibility temperature, as well as appreciably lower volatility compared to dioctyl phthalate. An additional factor which is advantageous in the product prepared by the present procedure is the fact that adulteration with branched aldehyde can be tolerated. Thus 2-propyl-4-methyl-hexyl phthalate has a low temperature flexibility value of −31.5 and the presence of 12% or so of this in the phthalate will only raise the low temperature flexibility, to about −38.5°, and the volatility is still excellent. By contrast dioctylphthakate would be more sensitive to adulteration by isomers as di(2-ethyl-4-methylpentyl) phthalate has a low temperature flexibility ($T_f$) of −30° C. and a very high volatility (6.7% in 1 day test.)

EXAMPLE 8

A phthalate plasticizer was prepared by using an alcohol mixture for esterification composed of 85% 2-propylheptanol, 11% 2-propyl-4-methylhexanol, and 4% 2-propyl-5-methylhexanol. The alcohol mixture was prepared in accord with procedures described herein, involving an aldol reaction of 75% n-pentanol, 25% 2-methylbutanal and 2% 3-methylbutanal, as obtainable from oxo reaction of butenes having a very small isobutylene content. The plasticizer with polyvinyl chloride (40% plasticizer) gave a low temperature flexibility ($T_f$) value of −38 to 31 39, 1 day volatility of 1.2% and 6-day volatility of 4.1–4.3%.

EXAMPLE 9

A mixture of 709 gm of n-pentanal, 237 gm of 2-methylbutanal and 19 gm of 3-methylbutanal was added over 40 minutes with stirring, to 300 ml of 1 molar potassium hydroxide solution at 88° C. After the addition was completed, the reaction mixture was maintained at 88° C. with stirring for a further 2 hours, at which time the n-pentanal was 96% converted. The aldol product consisted of 83% 2-propylheptanal, 13% 2-propyl-4-methylhexanal and 4% 2-propyl-5-methylhexanal. The reaction mixture also contained 75% of the originally charged 2-methylbutanal.

The reaction product was cooled and the organic phase was separated and hydrogenated at 160° C. under 1500 psi of hydrogen pressure in the presence of a cobalt on kieselguhr catalyst. The hydrogenation of the enals produced the corresponding alkanols, and the resulting mixture of $C_5$ alcohols and $C_{10}$ alcohols was separated by distillation and the $C_{10}$ alcohol was converted to its phthalate ester for use as a plasticizer.

EXAMPLE 10

Dimerization of propylene over transition metal catalysts produces a mixture of hexenes.

The linear hexenes in the mixture can be separated and such linear hexenes are for the most part 2-hexenes. The following procedure illustrates the reaction of 2-hexenes in an oxo reaction, followed by an aldol reaction of the product. A sample of refinery 2-hexenes was passed through basic alumina particles for removal of oxides and 802 grams of the hexenes was placed in a 1 gallon stainless steel autoclave with 4.75 grams $Co_2(CO)_8$ catalyst. The autoclave was pressure to 2400 psi gauge with 1:1 carbon monoxide and hydrogen, and heated to 110° C. The temperature was kept at about 110° C. for 1 hour and then rose to about 130° as the procedure was continued for about 5 hours. A 916.5 gram product was obtained, with conversion about 94% with about 78% selectivity to $C_7$ compounds, and 71.5% to $C_7$ aldehydes. Chromatography indicated the aldehydes were in ratio of about 29.4 n-heptanal to 16.7 2-methylhexanal to 8.5 2-ethylpentanal. A 907 gram amount of the product was distilled, with a final pot temperature of 120° C. and vacuum of 3 mm Hg. to obtain a 608 gram distillation fraction and 278 gram residue. Chromatography indicated the fraction included $C_7$ aldehydes in ratio 33.4 n-heptanal to 26.8 2-methylhexanal to 17.2 2-ethylpentanal, and minor amounts of other components. Evidently there was more loss of the normal aldehyde than the branched ones in the distillation.

It is feasible to achieve a higher percentage of n-aldehyde than present in the above distillation fraction, such as 60% or better, and therefore n-heptanal was added to the above fraction to have a more typical aldehyde for aldol reaction, about 600 grams of the above fraction being used with 500 grams n-heptanol. A 300 ml amount of 0.8 molar sodium hydroxide was placed in a reaction flask with 955 ml methanol, and the aldehydes were placed in an addition funnel. The reaction medium was heated to about 71° C., and addition was slowly started and completed in about 13 hours. Chromatography indicated about 50% completion of the reaction, with $C_{14}$ aldehydes in ratio of about 23.4% 2-pentylnon-2-enal to 8.72% 2-pentyl-4-methyloct-2-enal to 1.4% 2-pentyl-4-ethylhept-2-enal. Several $C_7$ aldehydes were also present in the ratio of 22.9 heptanal to 8.5 2-methylhexanl to 5.3 2-ethylpentanal.

The aldol condensation product was hydrogenated over a cobalt/kieselguhr catalyst, using 131 grams catalyst with 1336 grams of the condensation product. The materials were maintained at about 160° C. and 1500 psi gauge of hydrogen for about two hours when reaction appeared complete. Reaction conditions were maintained for an additional 4.5 hours. Analysis indicated about 99% completion of the hydrogenation. The product contained 2-pentylnonanol in about 18.4 to 7.2 ratio to a mixture of 2-pentyl-5-methyl-octanol and 2-pentyl-4-ethylheptanol and large amounts of $C_7$ alcohols from the unreacted aldehyde, being heptanol in a 27.5 to 16.3 ratio to a mixture of 2-methylhexanol and 2-ethylpentanol. The product was fractionated by distillation, with a 280 gram fraction being obtained at 110°–115° C. at 2 mm Hg from 1180 grams of hydrogenation product. The fraction was in large predominance composed of $C_{14}$ alcohols.

EXAMPLE 11

A mixture of hexenes produced by the Dimersol ® dimerization process was utilized as olefin reactant. The crude hexene cut from the dimerization was used, and had the distribution of linear and branched hexenes typical of such material. A 1029 gram amount of the hexenes was used in a 1 gallon autoclave with 6.04 grams catalyst, $Co_2(CO)_8$, 0.02 weight %. Peroxides had been removed from the hexenes by treatment on a basic alumina column. The autoclave was taken to reaction conditions with 1:1 $CO/H_2$ and maintained at 110° C. and 2600 psi gauge for 9 hours, with 80% of theoretical gas uptake, and then continued overnight. Chromatography indicated high conversion to $C_7$ aldehydes, with minor amounts of residual hexenes. A 1360 gram amount of the product was subjected to distillation, with a 797 gram fraction being obtained at pot temperatures of 60° to 97° C. as the vacuum dropped from 90 mm Hg to 5 mm Hg. Chromatography indicated a high portion of $C_7$ aldehydes with a very small amount of $C_6$ olefins.

A 792 gram amount of the above aldehyde fraction was utilized in an aldol reaction, adding the aldehyde material from an addition funnel to a reaction flask containing 564 grams methanol and 250.9 grams 0.8 molar sodium hydroxide. The addition took about 6 hours, with stirring at about 500 rpm and temperature at 72°–73° C. The reaction mixture was then refluxed for 1.5 hours. Analysis of a sample indicated only about 1 part aldol product to 3 parts aldehyde, on a mole basis. The reaction was continued at reflux overnight, giving 1 part aldol product to about 2.6 parts aldehyde reactant. During the reaction it was observed that the reaction mixture had a large upper phase and a smaller lower phase, indicating that methanol was not very effective in promoting miscibility and reaction, possibly because of the relatively long chain length of $C_7$ aldehydes. Chromatography showed a fair amount of the $C_{14}$ aldol product, including 2-pentylnonenal, and a large amount of unreacted $C_7$ aldehydes.

The above aldol product was subjected to further aldol reaction, after removing the methanol to employ different conditions. A 552 gram amount of the aldol condensate, 55.6 area percent $C_7$ aldehydes and 31.5 area percent $C_{14}$ enals, was placed in an addition funnel and added to a reaction flask containing 163 grams 0.8 M NaOH and 389 grams 2,5-hexanediol. Addition was complete after 45 minutes, with temperature maintained at 100° C. with agitation of the reaction mixture. The reaction mixture was then refluxed at 100° C. for 1.75 hours. The reaction mixture separated into upper and lower phases of about equal weight. The conversion had been improved in that the ratio of $C_{14}$ enals to $C_7$ aldehydes in the product (upper phase) was now about 1.7 to 1.

A 515 gram amount of the product was subjected to hydrogenation, employing 51.65 grams cobalt/kieselguhr catalyst and 160° C., about 1580 psi gauge hydrogen. Approximately 549 grams of product was recovered. The conversion of $C_{14}$ enals to $C_{14}$ saturated alcohols was about 90%, with about 10% found as unsaturated alcohols. The product was filtered to remove catalyst, and the filtrate was distilled. The process produced several $C_{14}$ alcohols in very substantial amounts, with a number of others in very small amounts. Several $C_7$ alcohols from unreacted aldehyde were also present in substantial amount.

The examples of procedures for converting propylene dimers, via oxo, aldol and hydrogenation, to $C_{14}$ alcohols, illustrate that the reaction is feasible, although conditions in the procedures are not optimized and results better than those reported can be achieved by appropriate determination of conditions. In the procedures it was found that a co-solvent, which can be referred to as a phase transfer solvent, such as a hexane diol, resulted in higher conversion in the aldol reaction than was obtained by the use of methanol. The diol apparently aids by providing greater solubility of the aldehyde reactants in catalyst-containing phase, thereby permitting more complete reaction. Other diols exhibiting appreciable solubility for both the reactants and aqueous catalyst system are expected to be similarly useful, and appropriate usage of such systems should make it possible to greatly exceed the 63% or so conversion obtained above, particularly when the aldehyde reactants contain very high proportions of aldehydes free of 2-substitution, as can be obtained by oxo reaction of the complete hexenes mixture obtained by propylene dimerization.

The hexenes product from a Dimersol ® dimerization refinery product was analyzed and found to have the following distribution.

| Hexene Distribution | |
|---|---|
| | % (100% Basis) |
| 2, 3-dimethyl-2butene | 6.4 |
| 2-methyl-2-pentene | 39.2 |
| trans-4-methyl-2-pentene | 15.9 |
| cis-4-methyl-2-pentene | 2.9 |
| 2-methyl-1-pentene | 5.0 |
| 2, 3-dimethyl-1-butene + 4-methyl pentene | 1.7 |

-continued

| Hexene Distribution | |
|---|---|
| | % (100% Basis) |
| trans-2-hexene | 16.5 |
| trans-3-hexene | 5.8 ⎫ |
| cis 3 + cis 2-hexene | 5.6 ⎬ 28.9 |
| 1-hexene | 1.0 ⎭ |

Dimersol dimerization process product and various hexene components thereof were reacted in an oxo variation over cobalt catalyst generally as described in Examples herein. The product distribution obtained are reported in Table 2 below, along with the reaction temperatures and times. The D-Mixture in the table is the mixture of all the hexenes obtained in the Dimersol dimerization process. The particular aldehydes are identified below the table by key to Roman numerals with the aldehyde group in all cases in the 1-position. The % aldolable product as reported includes all aldehyde products except those with 2-substituents.

amounts, apparently reacts readily in an aldol reaction to give suitable product.

The Dimersol® dimerization process has been referred to in various publications, e.g. see "How First Dimersol is Working" by Benedek et al, Hydrocarbon Processing, May 1980, page 143; also Chauvin et al, "The IFP Dimersol® Process for the Dimerization of $C_3$ and $C_4$ Olefinic Cuts", Advances in Petrochemical Technology, presented at American Institute of Chemical Engineers, Apr. 13, 1976, Kansas City, Mo.

The combination of the Dimersol® dimerization process, oxo process, aldol and hydrogenation provides a very efficient route from propylenes to detergent range alcohols. One of the known routes to such alcohols relies upon oligomerization of ethylene to obtain higher molecular weight materials which are then subjected to an oxo reaction. The presently proposed route is in many respects more efficient and economical than those involving ethylene oligomerization, as propylene costs less than ethylene, and the reactions involved using dimerization, oxo and aldol are more straight

TABLE 2

| | | | Oxo Product Distribution | | | | | | | | | |
|---|---|---|---|---|---|---|---|---|---|---|---|---|
| | Temp. | Run Time | % | | | | | | | | | % |
| Hexene | (°C.) | (hours) | I | II | III | IV | V | VI | VII | VIII | IX | Aldolable* |
| D-Mixture | 110 | 23 | 15.3 | 19.4 | 8.7 | 39.1 | 4.4 | 3.1 | 1.4 | 7.5 | 1.0 | 76.9 |
| D-Mixture | 130 | 4 | 14.9 | 25.0 | 8.5 | 36.2 | 4.3 | 1.8 | 1.1 | 7.4 | 0.8 | 77.9 |
| D-Mixture | | 3 | 15.4 | 23.5 | 8.8 | 37.9 | 4.5 | 0.7 | 1.1 | 7.5 | 0.7 | 77.5 |
| D-Mixture | | 2 | 16.8 | 25.5 | 9.6 | 33.8 | 4.9 | 0.8 | 1.0 | 7.2 | 0.6 | 76.9 |
| D-Mixture | | 1 | 18.8 | 24.5 | 10.7 | 31.8 | 5.4 | trace | 1.4 | 6.8 | 0.5 | 75.1 |
| 2-methyl-2-pentene | 116 | 3 | — | 34.3 | — | 56.6 | — | — | 1.3 | 6.9 | 0.9 | 90.9 |
| 2-methyl-2-pentene | 130 | 3 | — | 33.6 | — | 56.6 | — | — | 1.4 | 7.2 | 1.2 | 90.2 |
| 2-methyl-1-pentene | 116 | 3 | — | 10.6 | — | 84.4 | — | — | 0.4 | 2.5 | 2.1 | 95.0 |
| 4-methyl-2-pentene | 130 | 3 | | 65.9 | | 17.3 | | trace | 1.6 | 15.3 | trace | 83.2 |
| | | 2 | | 65.1 | | 16.6 | | | 1.6 | 16.8 | trace | 81.7 |
| | | 1 | | 67.6 | | 14.2 | | | 1.4 | 16.8 | trace | 81.8 |

I = heptanal
II = 5-methylhexanal
III = 2-methylhexanal
IV = 3-methylhexanal
V = 2-ethylpentanal
VI = 3,4-dimethylpentanal
VII = 2,-ethyl-3-methylbutanal
VIII = 2,4-dimethylpentanal
IX = 2,2-dimethylpentanal It will be noted that, despite the branching in the dimerization product mixture, very high selectivities to "aldolable" aldehydes are obtained, such as better than 75%. The result is even more pronounced when individual branched olefins are reacted, even when the methyl branches are located on an unsaturated carbon atom. Use of a catalyst which permits migration of the double bond, as the cobalt catalysts herein, is essential to this result.

One of the components found in the dimerization product mixture, 2,3-dimethyl--butene, is relatively unreactive in the oxo reaction, so, if desired the reaction can be effected to leave it unreacted.

With further regard to the aldehydes obtained by oxo reaction of propylene dimerization product, one of the isomers present in large amount is 3-methylhexanal. This aldehyde reacts readily in the aldol condensation. Moreover, in cross-aldol with n-heptanal, it appears to exhibit a very strong preference for the condensation to occur on the 2-carbon of the normal aldehyde, i.e. to produce 2-pentyl-5-methyloctanal, rather than 2(1-methylbutyl)nonanal. The latter compound, having adjacent methyl substituents, might be more resistant to biodegradation when converted to a detergent alcohol. The 5-methylhexanal, also obtained in substantial forward than an oligomerization which can produce a broad mixture of products and require extensive equipment and procedures to direct it to suitable product. As discussed hereinabove, the mixture of isomers obtained from a dimerization can be carried through the oxo, aldol and hydrogenation reactions to obtain high overall conversions and yields, despite the presence of extensive branching in the materials. It is fortunate to find that a high proportion of the materials are capable of taking part sequentially in all of the required reactions, and in particular that the aldehyde failing to react in the aldol reaction, because of 2-substitution, is at a comparatively low level.

It has also been found that pentenes can be hydroformylated to hexanals, and the hexanals condensed in an aldol reaction and hydrogenated to form 12-carbon alcohols, in a manner similar to such reactions with the hexenes.

The processes herein can employ various olefins as starting material and the conditions of the various oxo, aldol etc. stages as described for butenes are generally applicable to the processes employing hexenes or other olefins as starting material. With particular reference to the oxo stage, it will be noted that cobalt catalyst is employed with the hexenes in order to promote migration of the olefinic bond and high selectivity to desired aldehyde isomers, such catalysts being for example $Co_2(CO)_8$ which may be equivalent to $HCo(CO)_4$ under reaction conditions, and $HCo(CO_3)$ (Phosphine ligand).

The $C_{14}$ or other detergent range alcohols produced by the present process can be readily converted to detergents by known procedures. Thus non-ionic detergents are prepared by reaction with ethylene oxide to have a desired number of ethoxyl groups, e.g. 6 to 10 or 12 or so. These, or other ethoxylated alcohol, possibly with 2 to 3 ethoxyl groups can be reacted to form an alcohol ether sulfate, having a sulfate anionic end group with a sodium ot other cation. The alcohols can also be reacted to prepare sulfate derivatives. The detergents thus prepared will have the requisite hydrophobic groups for detergent properties. Moreover, the structures are such as to provide biodegradability, in that the structures are acyclic alkyl groups which are essentially free of any tertiary carbon groups and in which branching on adjacent carbon atoms is absent or at a very low level. The common 2-branching characteristic of aldol product, with or without various additional methyl or other lower alkyl branches in nonadjacent positions, is not expected to have any important effect on the biodegradable nature of the compounds. An alcohol ether sulfate prepared from 2-pentylnonanol has been described as biodegradable by Cranland et al, Surfactant Congress No. 4, Vol. 1, page 93 (1967). Also Kravetz et al, Proceedings of the American Oil Chemists' Society, 69th annual meeting, May, 1978, St. Louis, Mo., concluded that variation of branching from 45% to 75% linear had no appreciable effect on biodegradation rates of primary alcohol ethoxylates, and make reference to 58% branching giving biodegradation at rates not appreciably different from zero branching. It is further of interest that Farnesol, a natural alcohol with branching, degrades somewhat slower than a straight chain alcohol, but still degrades at a rate sufficient to meet stringent biodegradability requirements. Farnesol is a 15 carbon alcohol with methyl branches at the 3, 7 and 11 positions.

EXAMPLE 12

A freshly distilled sample of 2-pentene was hydroformylated in a 300 ml autoclave, employing 0.41 gram $(Co(CO)_8$ catalyst with 65.84 grams pentene. A 1:1 mixture of $CO/H_2$ was used, with initial charge to 1500 psi gauge and heating to 120° C. and 3000 psi. with agitation at 1000 rpm. Gas-uptake was observed, as the pressure was increased to 3000 psi. After about 2 hours, an 83 gram product was obtained. Chromatography showed a small residual amount of pentene and $C_6$ aldehydes in the ratio of 61.1 hexanal to 28.9 2-methylpentanal to 10.0 2-ethylbutanal. An aldehyde sample was provided to have aldehydes in the same ratio, using 189.1 grams hexanal, 89.9 grams 2-methylpentanal, and 31 grams 2-ethylbutanal, and placed in an addition funnel for addition to 110 ml of 0.8 M NaOH in a round bottom flask equipped with a mechanical stirrer. Heating was begun and addition was started after about 15 minutes and continued as reflux started around 91° C. Addition was completed in about 40 minutes. Stirring was continued for an hour, but without further heating, and a sample was taken. Analysis indicated partial reaction. The reaction mixture was heated to 95° C. for an additional 1½ hours. Upper and lower phases of the reaction mixture were separated, and the upper phase was analyzed. The analysis indicated better than 25% conversion to $C_{12}$ enal, nearly all being 2-butyloctanal, and large amounts of unreacted $C_6$ aldehydes, the major part of which was branched aldehydes. The aldehyde mixture can readily be hydrogenated to the corresponding alcohols.

EXAMPLE 13

An aldol procedure was carried out as in Example 12, except that the amount of water was increased ten fold. The same amount of NaOH was present, although now in much more dilute solution. Because of the large volume, less effective stirring was achieved. After a two hour reaction, analysis indicated substantial conversion to $C_{12}$ enals, although somewhat lower than in Example 12.

EXAMPLE 14

An aldol reaction was carried out as in Example 12, employing 6.1 to 2.9 to 1 ratio of hexanal to 2-methylpentanal to 2-ethylbutanal, the total amount being 310 grams. The branched aldehydes were placed in a flask with 110 ml of 0.8 M NaOH, and tetrabutylammonium chloride in an amount molecularly equivalent to the NaOH. The tetrabutyl-ammonium chloride serves as a phase transfer catalyst. The reaction flask was heated to reflux and addition was started. The addition continued for about 6 hours with reflux temperatures (pot) from 90°-95° C. The mixture was cooled and separated into two phases. Analysis of the upper phase showed better than 75% conversion to $C_{12}$ enals, about half of which was 2-butyloctenal, and the remainder mainly a mixture of 2-butyl-4-ethylheptanal and 2-butyl-4-ethylhexenal. In the unreacted $C_6$ aldehydes present, the branched aldehydes were in greater amount than the hexanal. The reaction can be directed to produce a higher percentage of product from the n-hexanal by adding the aldehydes together, rather than adding the n-aldehyde to the branched aldehydes in the reaction mixture as in the foregoing procedure. The phase transfer catalyst was effective in improving conversion in this procedure, but use of co-solvents, such as methanol or diols, may be more practical for large scale continuous operations. The use of hexanediol has been shown effective for aldol reaction of heptanals herein, and can similarly be used with hexanals.

It will be noted that the alcohols produced from both the pentenes and hexenes feedstocks are intended for use as detergent range alcohols. The considerations herein as to reaction conditions and various parameters of the oxo and aldol reactions as described for the hexenes and resulting $C_7$ aldehydes also are in general applicable to the pentenes and resulting $C_6$ aldehydes. The $C_{12}$ alcohols produced from the reactions starting with pentenes will have the hydrophobic groups such alcohols provide in detergents, and the groups will have a degree of branching similar to that of $C_{14}$ alcohols from hexenes. It is feasible to substantially avoid presence of branches on adjacent carbon atoms. In one particular aspect the present invention is directed to a process of preparing alcohols from an oxo reaction with olefins selected from those having 5 to 6 carbon atoms, or mixtures thereof, to obtain aldehydes having 6 to 7 carbon atoms, comprising high amounts of α-aldehydealkanes, and effecting aldol conversion with limited participation of 2-substituted aldehyde to obtain aldol product, which is then hydrogenated to $C_{12}$ or C14 alcohols having properties valuable for use in detergents.

What is claimed is:

1. A process of preparing alcohols which comprises conducting an oxo reaction with hydrogen, carbon monoxide and olefins selected from those having 3 to 7 carbon atoms to obtain aldehydes having from 4 to 8 carbon atoms and comprised of a mixture of isomer containing at least 50% alkanals with no branching at the 2-position and subjecting the aldehydes to an aldol reaction to cause good conversion of the aldehydes to aldol product but with that produced from cross-aldol of 2-substituted aldehydes constituting no more than 20% of the product, and hydrogenating to obtain alcohols.

2. The process of claim 1 in which the aldehydes have content of alkanals with no branching at the 2-position from about 60 to about 80% and the conversions of aldehyde to aldol product are in the range of about 75% to about 90%.

3. The process of claim 1 in which the conversion of aldehyde other than 2-substituted aldehyde in the aldol reaction is at least about 95%.

4. The process of claim 1 in which the oxo reaction is conducted with hydrogen and carbon monoxide at temperatures in the range of 80° to 150° C. and pressures sufficient to maintain catalyst stability but not over 5000 psi, and the aldol reaction is conducted in aqueous alkaline medium at temperatures of 60° to 150° C.

5. The process of claim 4 in which a cobalt catalyst is employed for the oxo reaction.

6. A method of preparing ten-carbon plasticizer alcohols which comprises conducting an oxo reaction at temperatures in the range of 80° to 150° C. and pressures sufficient to maintain catalyst stability but not over 5000 psi. with mixed butenes and hydrogen and carbon monoxide to obtain amyl aldehydes with at least about 66% n-pentanal content, and subjecting the amyl aldehyde mixture to an aldol reaction in aqueous alkaline medium at temperatures of 60° to 150° C. to cause at least about 80% conversion to aldol products comprising at least about 80% of the aldol product of n-pentaldehyde and no more than 20% of cross aldol product of n-pentanal with other aldehydes, hydrogenating to alcohols with hydrogen to obtain mainly 2-propylheptanol along with 2-propyl-4-methylhexanol and 2-methylbutanol and separating the alcohols from the reaction mixture, obtaining a ten-carbon atom plasticizer alcohol containing at least about 80% 2-propylheptanol and adapted to contribute good plasticizer properties to a phthalate diester prepared therefrom.

7. A process of preparing a plasticizer alcohol comprised of 2-propylheptanol and no more than 15% of 2-propyl-4-methylhexanol which comprises conducting an oxo reaction at temperatures in the range of 80° to 150° C. and pressures sufficient to maintain catalyst stability but not over 5000 psi. with a mixture of normal butenes and hydrogen and carbon monoxide to obtain a mixture of amyl aldehydes with at least about 66% n-pentanal content and without separation of aldehyde isomers conducting an aldol reaction in aqueous alkaline medium at temperatures of 60° to 150° C. of the mixture to convert a high percentage of such aldehydes to ten-carbon aldol products but stopping the reaction short of complete conversion so that substantially all of the n-pentanal has formed aldol product but a portion of the branched aldehyde in the aldehyde mixture is not reacted, hydrogenating the resulting aldehyde mixture with hydrogen and obtaining a 2-propylheptanol product in which the 2-propyl-4-methylhexanol co-product constitutes no more than about 15% of the 10-carbon alcohol composition, in admixture with 2-methylbutanol.

8. The process of claim 7 in which the 2-propyl-4-methylhexanol constitutes about 11–12%.

9. The process of preparing ten-carbon plasticizer alcohols which comprises conducting an oxo reaction at temperatures in the range of 80° to 150° C. and pressures sufficient to maintain catalyst stability but not over 5000 psi. of normal butenes and hydrogen and carbon monoxide to obtain aldehydes which are at least about 70% n-pentanal and subjecting the aldehydes to an aldol reaction in aqueous alkali of about 1 to 10% concentration by weight to cause nearly all of the n-petanal to be condensed, producing ten-carbon enals comprised of at least about 85% of 2-propylheptenal, and hydrogenating the 10-carbon enals with hydrogen to obtain alcohols comprised of at least about 85% 2-propylheptanol, and a substantial portion up to about 15% of other ten-carbon atom isomeric alcohols.

10. The process of claim 9 in which the oxo process is conducted at 1000 to 4000 psi in the presence of cobalt catalyst, and the aldol reaction is conducted at about 90° to about 130° C.

11. The process of claim 9 in which the amyl aldehydes are comprised of 70 to 85% n-pentanal and the ten-carbon alcohols are 85 to 95% 2-propylheptanol.

12. The process of preparing ten-carbon plasticizer alcohols which comprises conducting an oxo reaction at temperatures in the range of 80° to 150° C. and pressures sufficient to maintain catalyst stability but not over 5000 psi of normal butenes and hydrogen and carbon monoxide and in which substantially linear butenes which are at least one-third 1-butene are hydroformylated by reaction with carbon monoxide and hydrogen over cobalt catalyst to obtain amyl aldehydes with n-pentanal:2-methylbutanal ratios in the range of about 2.8:1 to 3.1:1, and the aldehydes are subjected to an aldol reaction in the presence of aqueous alkali hydroxide of about 1 to 10% concentration by weight, constituting about 15% to 75% by volume of the aqueous alkali and aldehyde reactant, at temperatures of about 90° to about 130° C. to condense nearly all of the n-pentanal while leaving some 2-methylbutanal unreacted to obtain ten-carbon enals with at least about 85% of 2-propylheptanal from self-condensation of n-pentanal, followed by hydrogentating the ten-carbon enals over hydrogenation catalyst with hydrogen at elevated pressure to obtain alcohols by reduction of enals and remaining amyl aldehydes, the ten-carbon alcohols obtained being composed of about 85 to 95% 2-propylheptanol and a substantial portion up to about 15% of other ten-carbon atom isomeric alcohols, and separating five-carbon alcohols and 10-carbon alcohols by distillation.

13. The process of preparing aldol products which comprises subjecting an amyl aldehyde mixture containing at least about 70% n-pentanal and a substantial amount of 2-methylbutanal to an aldol reaction with strong alkaline catalyst at temperatures of 90° to 130° C. to cause substantially all of the n-pentaldehyde to react, stopping the reaction with unconverted 2-methylbutanal still present and producing ten-carbon enals composed of at least about 85% 2-propylheptenal.

14. The process of claim 12 in which the hydrogenation is conducted at pressures above 500 psi. and temperatures above about 130° C.

15. A process of preparing alcohols which comprises conducting an oxo reaction with hydrogen carbon monoxide and a hexene mixture comprised mainly of methylpentenes with internal unsaturation with no more than 30% linear hexenes, so as to obtain $C_7$ aldehydes with less than 30% 2-substituted aldehydes subjecting the aldehydes to an aldol reaction to obtain aldol product with conversion of at least 70% and hydrogenation with hydrogen to obtain alcohols.

16. The process of claim 15 in which no more than one-third of the 2-substituted aldehydes are converted to aldol product.

17. The process of claim 15 in which the hexene mixture comprises substantially the hexenes mixture from a dimerization of propylene over a nickel and aluminum alkyl catalyst.

18. The process of claim 15 in which $C_{14}$ alcohols are produced with 2-pentyl-7-methyloctanol being the isomer present in largest amount.

19. The process of claim 15 in which more than 75% of the $C_{14}$ alcohol product has double branching but has practically no branches located on adjacent carbon atoms.

20. The process of claim 15 in which the oxo reaction is conducted with cobalt catalyst and hydrogen and carbon monoxide at temperatures in the range of 80° to 150° C. and pressures sufficient to maintain catalyst stability but not over 5000 psi, and the aldol reaction is conducted in aqueous alkaline medium at temperatures of 60° to 150° C.

21. The process of preparing alcohols in which substantially linear hexenes are separated from a propylene dimerization mixture and subjected to an oxo reaction with hydrogen and carbon monoxide to obtain better than 50% selectivity to alkanals with no branching at the 2-position and subjecting the oxo reaction product to an aldol reaction to produce an aldol product with no more than about 15% content from cross aldol of 2-substituted aldehydes, and hydrogenating with hydrogen to produce alcohols.

22. The process of claim 21 in which the product contains at least 85% 2-pentylnonanol and no more than about 15% 2-pentyl-4-methyloctanol.

23. The process of preparing aldol products which comprises subjecting a $C_7$ aldehyde mixture of isomers comprising at least 50% methylhexanals but no more than 30% of 2-substituted aldehydes to an aldol reaction with strong alkaline catalyst to effect high conversion of the methylhexanals to aldol product but with no more than one-half of the 2-substituted aldehydes being converted to aldol product.

* * * * *